United States Patent
Dalal et al.

(10) Patent No.: US 10,064,569 B2
(45) Date of Patent: Sep. 4, 2018

(54) DISPLACEMENT FEEDBACK DEVICE AND METHOD FOR SENSING OR THERAPY DELIVERY PROBES

(75) Inventors: Sandeep M. Dalal, Cortlandt Manor, NY (US); Cynthia Ming-Fu Kung, New York, NY (US); Shriram Sethuraman, Briarcliff Manor, NY (US); Jochen Kruecker, Washington DC, DC (US)

(73) Assignee: Koninklijke Philips N.V., Eindhoven (NL)

( * ) Notice: Subject to any disclaimer, the term of this patent is extended or adjusted under 35 U.S.C. 154(b) by 748 days.

(21) Appl. No.: 14/236,112

(22) PCT Filed: Jul. 30, 2012

(86) PCT No.: PCT/IB2012/053876
§ 371 (c)(1),
(2), (4) Date: Jan. 30, 2014

(87) PCT Pub. No.: WO2013/021310
PCT Pub. Date: Feb. 14, 2013

(65) Prior Publication Data
US 2014/0171792 A1 Jun. 19, 2014

Related U.S. Application Data

(60) Provisional application No. 61/521,499, filed on Aug. 9, 2011.

(51) Int. Cl.
*A61B 5/05* (2006.01)
*A61B 5/06* (2006.01)
(Continued)

(52) U.S. Cl.
CPC .......... *A61B 5/065* (2013.01); *A61B 17/3403* (2013.01); *A61B 2090/061* (2016.02); *A61B 2090/062* (2016.02); *F04C 2270/041* (2013.01)

(58) Field of Classification Search
CPC ....................................................... A61B 5/05
(Continued)

(56) References Cited

U.S. PATENT DOCUMENTS

| 5,598,269 A | 1/1997 | Kitaevich et al. |
| 6,120,465 A | 9/2000 | Guthrie et al. |

(Continued)

FOREIGN PATENT DOCUMENTS

| EP | 1649823 | 4/2006 |
| EP | 1864624 | 12/2007 |

(Continued)

OTHER PUBLICATIONS

Palasz, Z. et al., "Investigation of normal and malignant laryngeal tissue by autofluorescence imaging technique", Auris Nasus Larynx, vol. 30, Issue 4, 2003, Abstract.

*Primary Examiner* — Joel F Brutus

(57) ABSTRACT

A device, system and method for accessing internal tissue include a probe (108) disposed on a distal end portion of a medical device and configured to be inserted into a body along a trajectory path. A sensor (102) is mounted on a displacement tracker portion (104) of the medical device which is disposed on a proximal end portion of the device. The sensor is configured to measure a distance parallel to the probe between the displacement tracker portion and a tissue surface such that a position of the probe is determinable relative to the tissue surface upon advance or retraction of the probe along the trajectory path.

15 Claims, 3 Drawing Sheets

(51) Int. Cl.
*A61B 17/34* (2006.01)
*A61B 90/00* (2016.01)

(58) Field of Classification Search
USPC .......................................................... 600/424
See application file for complete search history.

(56) References Cited

U.S. PATENT DOCUMENTS

| | | | |
|---|---|---|---|
| 6,129,669 A * | 10/2000 | Panescu et al. | ............ 600/424 |
| 7,341,583 B2 | 3/2008 | Shiono et al. | |
| 7,428,048 B1 | 9/2008 | Farkas et al. | |
| 7,452,357 B2 | 11/2008 | Vlegele et al. | |
| 7,787,923 B2 | 8/2010 | Alarcon et al. | |
| 8,573,966 B2 | 11/2013 | Ehara et al. | |
| 9,179,845 B2 | 11/2015 | Farey et al. | |
| 2003/0045798 A1 | 3/2003 | Hular et al. | |
| 2004/0127894 A1 | 7/2004 | Eick et al. | |
| 2006/0089624 A1 * | 4/2006 | Voegele et al. | .................. 606/1 |
| 2007/0118100 A1 | 5/2007 | Mahesh et al. | |
| 2008/0091257 A1 | 4/2008 | Andreas et al. | |
| 2008/0195128 A1 | 8/2008 | Orbay et al. | |
| 2008/0275465 A1 | 11/2008 | Paul et al. | |
| 2009/0240273 A1 | 9/2009 | Decarlo | |
| 2010/0274239 A1 | 10/2010 | Paul et al. | |
| 2012/0116234 A1 | 5/2012 | Farey et al. | |

FOREIGN PATENT DOCUMENTS

| | | |
|---|---|---|
| EP | 1932477 | 6/2008 |
| FR | 2948007 | 1/2011 |
| JP | 2000287986 A | 10/2000 |
| JP | 2003159331 A | 6/2003 |
| JP | 2005323669 A | 11/2005 |
| JP | 2012081102 A | 4/2012 |
| WO | WO199933394 | 7/1999 |
| WO | WO200019919 | 4/2000 |
| WO | WO2003020119 | 3/2003 |

* cited by examiner

DISPLACEMENT FEEDBACK DEVICE AND METHOD FOR SENSING OR THERAPY DELIVERY PROBES

CROSS-REFERENCE TO PRIOR APPLICATIONS

This application is the U.S. National Phase application under 35 U.S.C. § 371 of International Application Serial No. PCT/IB2012/053876, filed on Jul. 30, 2012, which claims the benefit of U.S. Provisional Application Ser. No. 61/521,499, filed on Aug. 9, 2011. These applications are hereby incorporated by reference herein.

This disclosure relates to medical devices and methods, and more particularly to systems and methods which employ position sensing probes for medical procedures and other applications.

Ablation procedures such as radio frequency ablation (RFA) have been increasingly performed in recent years as an alternative to more invasive surgical procedures. During RFA, an electrode with un-insulated tip is inserted into a tumor or lesion to be ablated under ultrasound, computed tomography (CT), X-ray or magnetic resonance imaging (MRI) guidance. When the electrode is placed, a radio frequency current is applied to the tip which creates tissue heating and cell death above 60° Celsius.

To treat tumors that are larger than a nominal ablated volume for a single ablation at a given needle position, the needle tip needs to be repeatedly repositioned to ablate different parts of the tumor, with the treated volumes partly overlapping each other. This process needs to be repeated until the entire tumor is covered by the set of ablations, also referred to as a "composite ablation".

An ablation probe is specified by its manufacturer to produce a nominally ablated volume, e.g., either a spherical or ellipsoidal shaped ablation under normal operating conditions. A clinician inserts the ablation probe from an entry point on the patient's skin that provides the best access to the tumor site. The clinician usually ablates at the most distal location (far from the entry point) in the tumor to ensure a complete ablation of the most distal zone of the tumor. The clinician then retracts the probe from the most distal location to a proximal location (nearer to the entry point) to ablate the tumor at the proximal end. Further advancement or retraction of the probe allows the clinician to ensure that the tumor is completely ablated taking into account the actual size of the tumor and associated margins that have to be included in the planned target volume (PTV) and the actual ablation sizes achieved in the procedure.

Ablation procedures typically employ either a single ablation probe or multiple probes inserted into a tumor. Single ablation probes are used to ablate a tumor in a sequential manner. A probe is inserted once into a target site, and an ablation is performed. Further ablations are performed after repositioning the same probe to a next target site. Currently, the selection of target locations within the PTV is typically done by "mental planning" methods. The clinician uses his/her best judgment on how to best place a cluster of ablations from the selected probe to optimally cover and treat the tumor, this requires the clinician to pick one or more entry points and optimal target ablation sites.

Alternately, computer-assisted planning tools can be used to determine the optimal target ablation sites. In this case, a planning algorithm computes and presents to the clinician a set of target sites, i.e., spatial locations in the tumor or its neighborhood where the RFA probe tip should be placed to get a composite set of ablations that optimally cover and treat a tumor.

When multiple ablation probes are used in a procedure, it may be advantageous to insert them from different orientations, i.e., using skin entry points that are not adjacent to each other. Multiple probe trajectories permit a clinician to avoid obstacles (e.g., ribs, critical organs, major blood vessels, etc.) for the probe tip to reach a target ablation location by choosing an alternative needle trajectory. Ablation probes from some manufacturers allow a clinician to simultaneously provide energy to the multiple probes to reduce time to ablate the entire tumor. In the case of multiple probes being used, the clinician has to place the probes at a set of target locations but then mentally determine and execute the necessary displacement to be applied to the probe tip locations so as to best ablate the entire tumor.

The probe tip is not always and not the only point of interest, for example, an active region (where the treatment energy is delivered from) of the probe may be offset from the probe tip by a distance. However, this active region's offset from the tip is precisely known by the manufacturing and design of the device. Therefore, if the tip location is known, the location of the active region is also known. The planning tools take this offset into account in tracking other points or regions during a procedure.

Computer assisted planning tools may also be used to determine the set of probe tip locations that are required to optimally ablate the tumor. The set of locations may be such that successive locations lie on a prescribed trajectory and only require the clinician to retract or advance the probe tip along the same trajectory by a specific distance.

In accordance with the present principles, a device, system and method for accessing internal tissue include a probe disposed on a distal end portion of a medical device and configured to be inserted into a body along a trajectory path. A sensor is mounted on a displacement tracker portion of the medical device which is disposed on a proximal end portion of the device. The sensor is configured to measure a distance parallel to the probe between the displacement tracker portion and a tissue surface such that a position of a probe tip is determinable relative to the tissue surface upon advance or retraction of the probe along the trajectory path.

A medical system includes a probe disposed on a distal end portion of a medical device and configured to be inserted into a body along a trajectory path. A sensor is mounted on a displacement tracker portion of the medical device and disposed on a proximal end portion of the device. The sensor is configured to measure a distance parallel to the probe between the displacement tracker portion and a tissue surface such that a position of the probe is determinable relative to the tissue surface upon advance or retraction of the probe along the trajectory path. A display is configured to display distance measurements gathered by the displacement tracker portion. An external computing component is coupled to the medical device through a communications link, the external computing component providing distance values for translating the probe along the trajectory path in accordance with a treatment plan.

A method includes determining a plan for accessing internal tissue; positioning a probe in accordance with a trajectory consistent with the plan; measuring a distance parallel to the probe along the trajectory between a proximal end portion of a medical device and a tissue surface to locate a first site for a portion of the probe; executing a medical action at the first site; and repositioning the probe in accordance with the trajectory by remeasuring the distance parallel to the probe along the trajectory between the proximal end portion of the medical device and the tissue surface to locate a subsequent site for the portion of the probe.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

Figure 1:
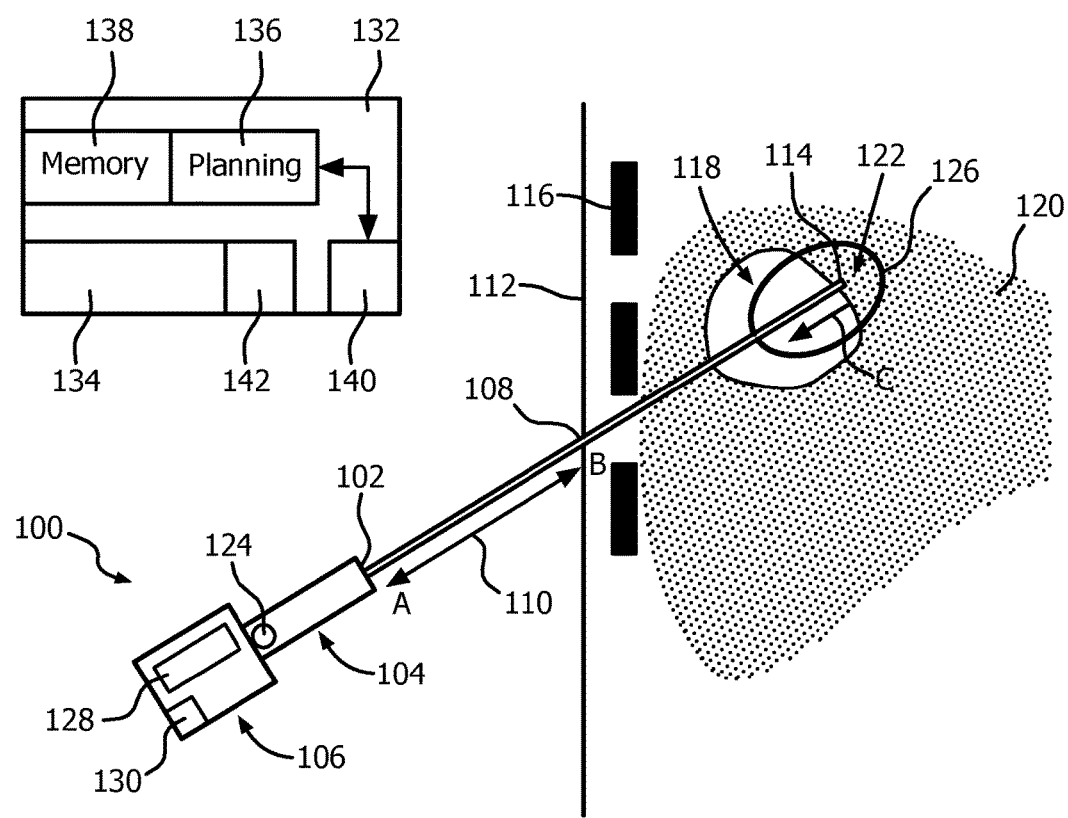
FIG. 1 is a schematic block diagram showing a medical system which employs a device configured for ablation which uses displacement feedback for carrying out a treatment plan in accordance with one illustrative embodiment.

The present disclosure describes systems and methods for radio frequency ablations (RFA) and/or other procedures. The present principles provide a way for a clinician to get feedback on a displacement of a probe as the probe is advanced or retracted initially or between successive ablations or other treatment procedures.

Using mental or computer-assisted planning tools a clinician is aware, or made aware, of an exact refraction or advancement displacement needed for the probe tip along a certain trajectory. The distances between successive ablations may be of the order of about 1-3 centimeters for typical ablation procedures. However, there is no physical means provided on a radio frequency (RF) probe that can measure the displacement of a probe tip between ablations and communicate that to the clinician during the procedure. To overcome that disadvantage the clinician may employ a simple means, e.g., a ruler to estimate the distance traveled by the handle when the clinician advances or refracts the probe. However this requires additional careful attention by the physician or assistant during the procedure. The probe itself may move slightly (e.g., the probe could enter deeper into the tissue due to its own weight) even after the clinician has repositioned the probe tip to the new target site. Therefore, the distance measurement becomes invalid and may lead to incorrect estimates of tumor coverage.

The present principles provide a displacement sensor on a displacement tracking device that is mounted on a probe, e.g., near a handle of the probe. The displacement sensor measures the distance between a point on the sensor and a point on a skin surface (distance between points) on a trajectory parallel to the needle. Displacement sensors based on fiber-optics or laser-based technologies may be employed. An accuracy of this type of sensor may be less than 1 mm, which is sufficient for probe tip displacement measurement in ablation procedures.

It should be understood that the present invention will be described in terms of medical instruments and in particular ablation instruments; however, the teachings of the present invention are much broader and are applicable to any instruments employed in destroying tissue using heat or heat generating techniques or cooling techniques, such as cryoablation and the like, biopsies, imaging, pathology probes or devices, etc. In particular, the present principles are applicable to procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The present principles are not limited to ablation probes and are applicable to any kind of biopsy, imaging, sensing, pathology or other types of probes that need precise placement of the probe tip inside the body to biopsy, image, sense, collect pathology samples, deliver treatment, etc. with multiple placements relative to a previous placement.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

Referring now to the drawings in which like numerals represent the same or similar elements and initially to FIG. 1, a surgical device 100 is shown in accordance with one illustrative embodiment. The device 100 includes a displacement emitter/sensor 102 mounted on a displacement tracking device 104. The displacement tracking device 104 may be mounted on or near a handle 106 of the device 100. The displacement tracking device 104 may include a signal emitter 102, such as a laser diode, ultrasonic source, electromagnetic (EM) field generator or other signal producing device to emit a signal (light, sound, EM, etc.) to reflect off of a skin surface 112 (or otherwise generate a measurable response) and be detected by a receiver or sensor 102. In the case of EM tracking, an EM tracker may be positioned at a position somewhere on the device 100 (e.g., in a probe 108). The signal emitter/receiver 102 (hereinafter referred to as sensor or displacement sensor) may include separate components (e.g., emitter and receiver) or be integrated into one unit (e.g., for a laser or Ultrasound based sensor). The signal emitter and receiver may be controlled by a controller on the displacement tracking device 104 or be controlled by an external computing device or component 132.

The device 100 includes a probe or needle 108, such as, e.g., a radio frequency (RF) probe, a biopsy needle, a needle for the administering of medicine, etc. The displacement sensor 102 is configured to measure a distance 110 between a point (A) on the sensor 102 and a point (B) on the skin surface 112 (e.g., a distance between points A and B). The distance A-B is preferably on a trajectory parallel to the probe 108 or needle. The sensor 102 may include a displacement sensor that is based on fiber-optics or laser-based technology. The accuracy of the sensor 102 is preferably better that about 1 mm and is sufficient for displacement measurements of a probe tip 114 (or other reference) in ablation or other procedures.

A reset button 124 may be disposed on the displacement tracking device 104. The reset button 124 permits a clinician to assign a current probe tip position for the tip 114 as a reference position, e.g., the currently measured distance is set to zero. This enables subsequent distance measurements to be calculated with respect to the reference position. In the case of performing ablations, the probe tip location at a first ablation site 122 serves as the reference position and ensures that the subsequent ablation is performed at a known displacement with respect to the first ablation site 122. The desired displacement from the first ablation site 122 is a value that is either mentally calculated by the clinician or determined by a computer-assisted planning algorithm that communicates the value to the clinician. Each time the clinician has completed an ablation at a current target site, the clinician can use the reset button 124 to indicate that the current ablation site can serve as the new reference position for a subsequent ablation. In addition to or instead of the ablation example, sequential positions may be determined for other procedure as well, e.g., a biopsy device, sensing device, other kinds of therapy delivery devices.

In one example, device 100 includes an ablation device having ablation electrodes disposed at or near the tip 114. A trajectory and entry point are computed manually or using a computer-assisted algorithm (e.g., a planning program 136). The plan also identifies precise spatial locations for the targets that are needed for the probe or needle to reach so as to successfully execute the medical procedure. The probe or needle 108 is then positioned and advanced into a patient through the entry point on the skin surface 112, in an illustrative example between ribs 116 or other obstructing tissues, and into an organ 120. The organ 120 may have a lesion or tumor 118 or other region of interest where an ablation or other activity is needed. Upon entering the skin 112, the reset button 124 may be activated to zero-out the measurement of the sensor 102. As the probe 108 is advanced or retracted the measurement will be updated so that the clinician knows how deep the tip has penetrated on the trajectory path. This provides an easy and accurate position determination for locating the first ablation site 122. Next, an ablation (or other procedure) is carried out at the first ablation site 122. An ablated region 126 results from the ablation. The first ablation site 122 is preferably at a most distal position (although other ablation position sequences may be employed). A second ablation site is determined by resetting the sensor measurement position and retracting the probe 108 in a direction of arrow "C" by an amount determined by a treatment plan.

In a particularly useful embodiment, a display 128 may be included on the handle 106 or on the displacement tracking device 104. The display 128 may include a simple liquid crystal display (LCD) or the like to display a measured numerical displacement at a specific resolution, e.g., 1.0 mm. Optionally, the display 128 could also show a computed distance to a next target site as communicated to the device 100 by a planning algorithm via a communications module 130. The clinician would then be able to view a required distance to the next target site, and the actual measured distance from the previous reference location. Other information and instructions may also be displayed on display 128. It should be understood that the display 128 may be mounted on another device and measurement signals from the device 100 may be communicated by the communication module 130 to another component 132 and displayed on a display 134 on that component 132.

The optional communications module 130 on the device 100 may receive data from the external computing device or component 132 that executes the planning program or algorithm 136 and keeps track of ablations as they are performed during the procedure. The component 132 preferably includes a processor 140 and a counterpart communication module 142 for communicating with the module 130. The module 130 preferably employs a wireless communications link for convenience. The communications module 130 receives a next ablation's displacement value with respect to a current ablation location and presents the value on the display 128 on the device 100 or on the display 134 on the component 132 (or both). In this way, the clinician would not have to review the planning algorithm's set of planned locations of the target sites to comprehend the current trajectory as well as the necessary displacement between subsequent ablation locations. The displacement values would be computed by the planning algorithm 136 stored in memory 138 and directly communicated to the display 128 using the communications module 130 on the device 100 having the probe 108. The clinician would not have to take his/her eyes off the correct execution of the ablation procedure since the displayed values are directly presented on the device 100 with the probe 108.

The communications module 130 offers the possibility of communicating the actual measured distance of the current probe tip position 114 relative to a reference position back to the planning algorithm 136 on the external computing device 132. This is useful in case the probe 108 slips or inadvertently moves from the planned target position, and the clinician does not correct this error prior to performing the ablation. The planning algorithm 136 could then be instructed to use an actual distance that the needle 108 has been retracted (or advanced) to update the spatial position of the new ablation. In the case of ablation procedures, this can have an impact on the optimally planned coverage of the PTV since the ablation probe 108 is not at the planned position. Adaptive planning may be employed that takes the actual spatial position of probe-tip placement and consequently the locations of the executed ablations into account and calculates new target locations for the probe as a result of this feedback. The displacement tracking of device 100 with the communications module 130 enables this type of feedback to be employed.

In one embodiment, a measurement sensor may include an electromagnetic (EM) tracker, which may be placed inside the device 100 or probe 108, and not necessarily at the proximal end (e.g., could be inside the tip 114 of the device 100) or at any other location. The displacement tracking device 104 or other component (e.g., component 132) may include an EM field generator, and the EM tracker may be employed as the sensor to measure displacements. The EM tracking may also be employed for additional guidance information or feedback, if desired.

In some embodiments, composite ablations may be performed with basic imaging guidance from ultrasound (US), computed tomography (CT), electromagnetic tracking, etc., but usually without navigation assistance and without quantitative or computerized planning. The results of the procedure largely depend on the intuition and experience of the clinician. The process of composite ablation planning and execution is difficult, and it has been pointed out that full coverage of a planning or planned target volume (PTV) with (smaller) individual ablations may need a large number of ablations.

The planned composite ablation should cover the PTV in an optimal fashion, i.e. with the minimum number of ablations (each ablation taking between 12 and 20 minutes) and providing optimal coverage of the tumor tissue while minimizing damage to healthy tissue. In accordance with the present principles accuracies in executing or placing the ablation probes according to a "mental plan" or computed plan is greatly improved. Use of the displacement tracking device 104 provides the possibility of any errors in positioning of the probe 108 to be taken into account by adaptive planning methods. The PTV coverage actually achieved with these methods is much more likely to eradicate the tumor, avoiding tumor recurrence and without causing excessive damage to healthy tissue surrounding the tumor.

Figure 2:
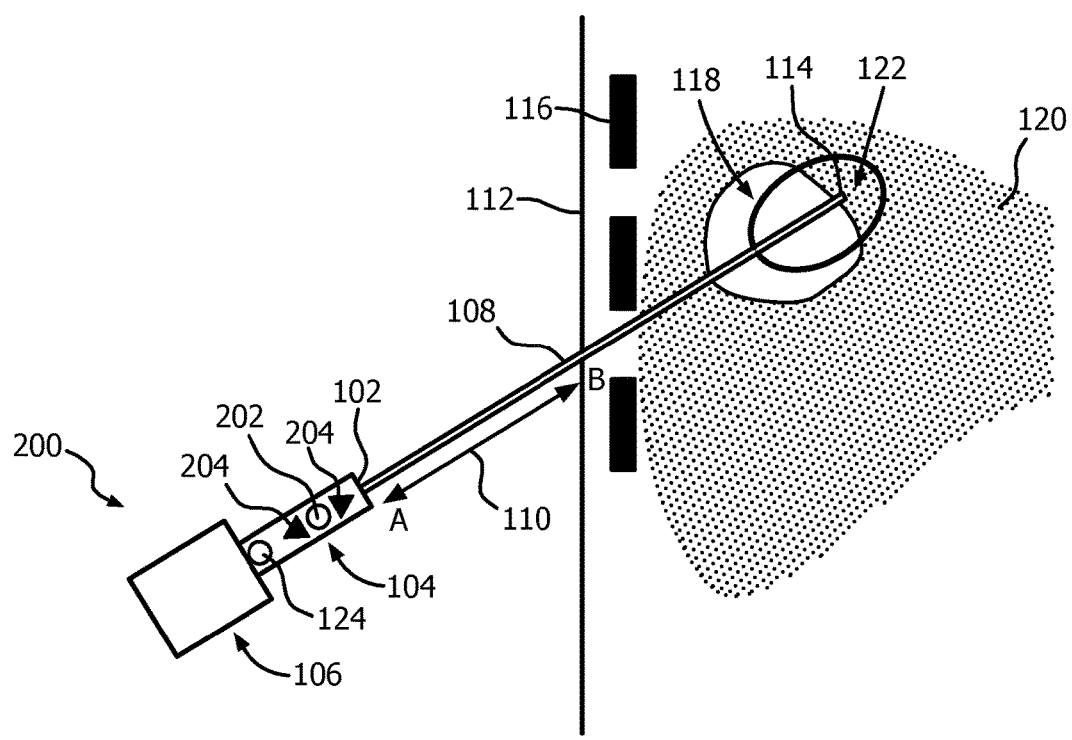
FIG. 2 is a schematic block diagram showing another medical system which employs a device configured for ablation which relays displacement feedback with an indicator for carrying out a treatment plan in accordance with another illustrative embodiment.

Referring to FIG. 2, another embodiment of a medical device 200 may include all or some of the same features as described with respect to FIG. 1. A simplified indicator 202 may be employed instead of or in addition to the display 128 of FIG. 1. The indicator 202 may include a visual, audible, vibrational, etc. scheme for indicating when the probe 108 has been advanced or retracted to a next computed treatment location.

For example, the indicator 202 may be a two color (e.g., red/green) indicator that offers feedback to the clinician on whether to retract or advance the needle without displaying a numerical distance. The green indicator lights when the clinician is at the target position within a certain tolerance (e.g., ±0.5 mm). Note that the same indications may be implemented using other means, e.g., audible sound, vibration, etc.

Assuming the communication module 130 (FIG. 1) is available and tracks the displacement to a next ablation position using the planning algorithm 136, it is possible to eliminate the numerical display device 128 (FIG. 1) showing the achieved displacement. This device can be replaced with the indicator 202, e.g., a set of simple red/green lighted indicators and/or lighted arrows 204 to provide feedback to the clinician if the probe needs to be retracted or advanced to reach the next target position.

The present principles may be implemented with different combinations of features. For example, one embodiment may be employed without the communications module 130. In this case, the clinician can see the measured distance to the skin 112 at all times, can press the reset button 124 when the ablation at the current site is completed and can know the necessary distance to a next ablation site or can see the result of the planning algorithm 136 to understand the next ablation that has to be performed and the necessary distance between the sites. Once the clinician moves the RF probe 108, the displacement sensor 102 provides feedback to continuously indicate the measured distance. The clinician positions the probe 108 when the distance is displayed (e.g., on display 128) by the displacement tracking device 104 that matches the necessary distance. At this point the clinician can perform the next ablation with confidence knowing that the location of the probe tip 114 at the new site matches the mentally planned or computer-planned location. In another embodiment, the device 100 includes the communications module 130. The display 128 can show additional information about the necessary distance to the next target as well as the actual measured distance from the previously set reference position.

In one particularly useful embodiment, the displacement tracking device 104 may be removed from one RF probe 108 and placed on a different RF probe. This makes the displacement tracking device 104 suitable for re-use in procedures with multiple probes or probe placements or across different patients. Since the displacement tracking device 104 does not contact the patient the displacement tracking device 104 remains in a sterile zone.

The present principles may be employed in a plurality of different applications. For example, the present principles can be applied to interventional oncology procedures, e.g., radiofrequency ablation, microwave ablation, cryoablation, etc. The present principles may be employed in procedures where the clinician directly determines where to place the RF probe tips—particularly when multiple probe tip locations are aligned on a single trajectory and require only a retraction or advancement of the probe tip by specific distances along the trajectory. The present principles may also be employed in procedures where ablation planning and navigation guidance software may be used to treat large, complex tumors using sequential application of a single ablation probe, or multiple ablation probes inserted and energized simultaneously from multiple access points. Ablation procedures are usually performed to treat tumors in, e.g., the liver, kidney, lung etc. The present principles may be employed in any other procedures as well, such as, e.g., one or more of sensing, biopsy, imaging, pathology, etc.

Figure 3:
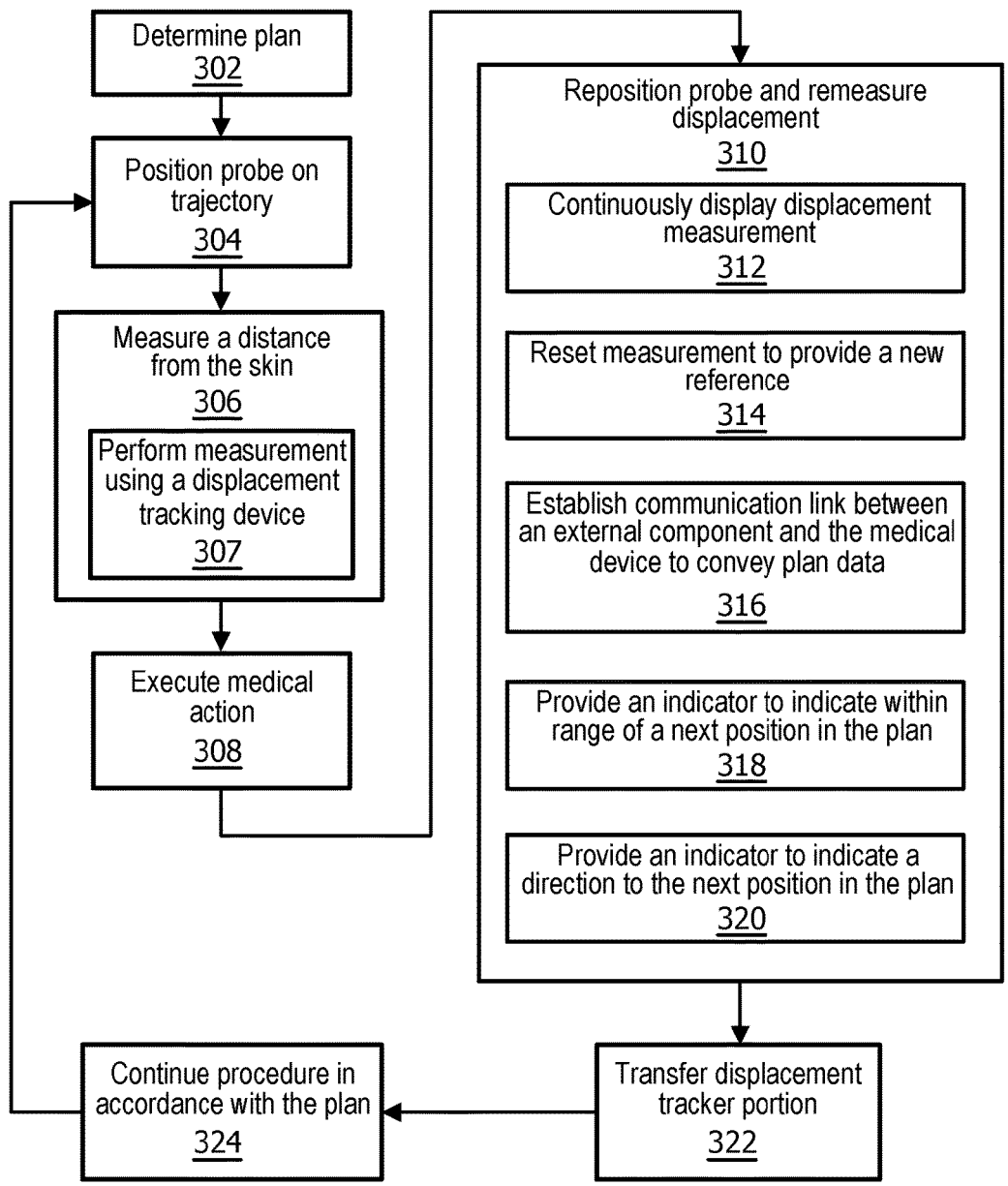
FIG. 3 is a flow diagram showing a method for accessing internal tissue in accordance with an illustrative embodiment.

Referring to FIG. 3, a method for accessing tissue using displacement feedback is shown in accordance with one embodiment. Accessing tissue may include ablation treatment, injecting medication, performing a biopsy, etc. using a probe, needle or other rigid instrument that enters the body of a patient with a portion remaining external to the patient. In block 302, a plan for accessing internal tissue is determined to perform the medical procedure. This may include a mental plan or a plan determined using a computer-assisted planning algorithm to provide treatment of a planned target volume or other target region. The plan preferably includes a trajectory that considers optimal access and treatment options. This may include mapping a path around bones, blood vessels, etc. to achieve the target region from an external entry point or points. The plan also identifies precise spatial locations for the targets that are needed for the probe or needle to reach so as to successfully execute the medical procedure. In block 304, a probe is positioned in accordance with the trajectory consistent with the plan. This may include a manual alignment or an alignment provided by a securing mechanism, a guide, a robot, a fixture or other device.

In block 306, a distance to a reference is measured, e.g., parallel to the probe, along the trajectory between a proximal end portion of a medical device and a tissue surface (or other reference) to locate a first site for a tip of the probe. The first site for the tip of the probe represents the first of the target sites determined by the plan 302. The measurement of the distance may be performed by a displacement tracking portion of the medical device in block 307. The displacement tracking portion may include a laser beam measurement, sonic or ultrasonic measurement, or other non-contact measurement system.

In block 308, a medical action is executed at the first site. This may include an ablation, administering medication, acquiring a biopsy specimen, sensing tissue temperature, analyzing tissue characteristics or other action. In block 310, the probe is repositioned in accordance with the trajectory by remeasuring the distance parallel to the probe along the trajectory between the proximal end portion of the medical device and the tissue surface to locate a subsequent site for a tip of the probe.

One or more of the following steps as shown in blocks 312-320 may be performed. In block 312, a measurement value is continuously displayed to track positional changes. This includes remeasuring where movement of the probe is tracked during advancement or withdrawal of the probe. In block 314, the measurement value can be reset at any time by activating a reset button mounted on a displacement tracker portion of the medical device. This may be employed to set a reference point against which a position for a next site (e.g., a next target ablation site on the current trajectory as per the plan 302) can be determined. In block 316, a communication link between a communications module on the medical device and a communications module on an external component is established such that information for locating the subsequent site is conveyed to the medical device over the communications link. The external computing component may store a planning algorithm configured to determine positions for subsequent treatment areas in accordance with the plan.

In block 318, an indicator may be provided on the medical device which indicates a first state when the probe tip is in a determined range and a second state when the probe tip is outside the determined range. In block 320, an indicator may be provided on the medical device which indicates a direction to move the probe tip to the subsequent site.

In block 322, the displacement tracking portion may be transferred between a plurality of probes. In this way, measurements can be made using a single displacement tracking portion for multiple probes or the displacement tracking portion may be reusable for different procedures and/or patients by discarding the probe and retaining the displacement tracking portion. In block 324, medical actions may continue in accordance with the plan.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for displacement feedback devices and methods for probes (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A medical device, comprising:
a probe disposed on a distal end portion of the device and configured to be inserted into a body along a trajectory path; and
a sensor mounted on a displacement tracker portion of the device and disposed on a proximal end portion of the device, the sensor configured to measure a distance parallel to the probe between the displacement tracker portion and a tissue surface which changes as the probe is advanced or retracted relative to the tissue surface, such that a position of the probe is determinable relative to the tissue surface upon advance or retraction of the probe along the trajectory path to determine a displacement from the position to a next position of the probe in the body.

2. The device as recited in claim 1, wherein the probe includes an ablation probe having one or more ablation electrodes formed thereon.

3. The device as recited in claim 1, further comprising a display that indicates a measurement value measured by the sensor.

4. The device as recited in claim 1, further comprising a reset button mounted on the displacement tracker portion to reset a measurement value.

5. The device as recited in claim 1, further comprising a communications module configured to communicate with an external component such that a position of the probe is monitored relative to a medical treatment plan.

6. The device as recited in claim 1, wherein the displacement tracker portion includes an indicator mounted thereon which indicates a first state when the portion of the probe is in a determined range and a second state when the portion of the probe is outside the determined range.

7. The device as recited in claim 1, wherein the displacement tracker portion includes an indicator mounted thereon which indicates a direction to move the probe for a subsequent operation.

8. The device as recited in claim 1, wherein the probe is employed for one or more of sensing, biopsy, imaging, or pathology.

9. A medical system, comprising:
a probe disposed on a distal end portion of a medical device and configured to be inserted into a body along a trajectory path;
a sensor mounted on a displacement tracker portion of the medical device and disposed on a proximal end portion of the device, the sensor configured to measure a distance parallel to the probe between the displacement tracker portion and a tissue surface which changes as the probe is advanced or retracted relative to the tissue surface, such that a position of the probe is determinable relative to the tissue surface upon advance or retraction of the probe along the trajectory path to determine a displacement from the position to a next position of the probe in the body;

a display configured to display distance measurements gathered by the displacement tracker portion; and an external computing component coupled to the medical device through a communications link, the external computing component providing distance values for translating the probe along the trajectory path in accordance with a treatment plan.

10. The system as recited in claim 9, wherein the display is provided on one or more of the medical device and the external component.

11. The system as recited in claim 9, wherein the external computing component stores a planning algorithm configured to determine positions for subsequent areas in accordance with the treatment plan.

12. A method, comprising:

determining a plan for accessing internal tissue;

positioning a probe in accordance with a trajectory consistent with the plan;

measuring a distance parallel to the probe along the trajectory between a proximal end portion of a medical device and a tissue surface which changes as the probe is advanced or retracted relative to the tissue surface to locate a first site for a portion of the probe;

executing a medical action at the first site; and repositioning the probe in accordance with the trajectory by remeasuring the distance parallel to the probe along the trajectory between the proximal end portion of the medical device and the tissue surface to determine a displacement from the first site to a subsequent site of the probe in the body to locate the subsequent site for the portion of the probe.

13. The method as recited in claim 12, further comprising resetting a measurement value by activating a reset button mounted on a displacement tracker portion of the medical device.

14. The method as recited in claim 12, further comprising establishing a communication link between a communications module on the medical device and a communications module on an external component such that information for locating the subsequent site is conveyed to the medical device over the communications link.

15. The method as recited in claim 12, further comprising providing an indicator on the medical device which indicates a first state when the portion of the probe is in a determined range and a second state when the portion of the probe is outside the determined range.

* * * * *